(12) United States Patent
Weiss et al.

(10) Patent No.: US 8,914,096 B2
(45) Date of Patent: Dec. 16, 2014

(54) ADAPTATION PROBE FOR INSERTION INTO IMPLANTED ELECTRODE DEVICES OF ACTIVE MEDICAL IMPLANTS AND SET COMPOSED OF AN IMPLANTABLE ELECTRODE DEVICE AND AN ADAPTATION PROBE

(75) Inventors: Ingo Weiss, Berlin (DE); Michael Friedrich, Kleinmachnow (DE); Stefan Knorr, Berlin (DE); René Fischer, Berlin (DE); Marc Steffen Schurr, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 610 days.

(21) Appl. No.: 13/018,132

(22) Filed: Jan. 31, 2011

(65) Prior Publication Data

US 2011/0196229 A1    Aug. 11, 2011

(30) Foreign Application Priority Data

Feb. 11, 2010   (DE) .......................... 10 2010 000 368
Feb. 11, 2010   (DE) .......................... 10 2010 000 370
Feb. 11, 2010   (DE) .......................... 10 2010 000 371
Feb. 11, 2010   (DE) .......................... 10 2010 000 372

(51) Int. Cl.
*A61N 1/08*    (2006.01)
*A61B 5/055*   (2006.01)
*A61N 1/05*    (2006.01)
*H03H 1/00*    (2006.01)
*H03H 7/01*    (2006.01)

(52) U.S. Cl.
CPC ............... *A61N 1/05* (2013.01); *H03H 1/0007* (2013.01); *H03H 7/0115* (2013.01); *A61N 2001/086* (2013.01); *H03H 7/1766* (2013.01)
USPC .............. 600/427; 600/423; 607/116; 607/37

(58) Field of Classification Search
CPC . A61N 1/05; A61N 2001/086; H03H 7/0115; H03H 7/1766; A03H 1/0007; G01R 33/34084; A61B 5/055; A61M 2025/09083
USPC ............ 600/423, 427, 433–435; 607/116, 37; 174/36
See application file for complete search history.

(56) References Cited

U.S. PATENT DOCUMENTS 6,628,980 B2   9/2003  Atalar et al.
7,363,090 B2   4/2008  Halperin
(Continued)

FOREIGN PATENT DOCUMENTS

WO      WO 03063954 A1    8/2003

OTHER PUBLICATIONS

European Search Report dated May 6, 2011 (6 pages).

*Primary Examiner* — Tammie K Heller
(74) *Attorney, Agent, or Firm* — ARC IP Law, PC; Joseph J. Mayo

(57) ABSTRACT

An adaptation probe for insertion into implanted electrode devices of active medical implants to enable them for use in high-frequency magnetic alternating fields of MRI systems comprises an elongated, flexible probe body, and at least one electrical assembly, which has one or more electrical components connected to an interface, in the probe body, and which can be electrically connected to a supply lead of the electrode device such that the electrically properties of the electrode device can be adapted, in particular the frequency-dependent resistance, impedance, capacitance, or inductance thereof.

18 Claims, 9 Drawing Sheets

(56) References Cited

U.S. PATENT DOCUMENTS

| | | |
|---|---|---|
| 2003/0083726 A1* | 5/2003 | Zeijlemaker et al. .......... 607/122 |
| 2003/0144721 A1* | 7/2003 | Villaseca et al. ............. 607/122 |
| 2004/0199071 A1 | 10/2004 | Lardo et al. |
| 2005/0222642 A1* | 10/2005 | Przybyszewski et al. ...... 607/48 |
| 2007/0112398 A1 | 5/2007 | Stevenson et al. |
| 2008/0116997 A1 | 5/2008 | Dabney et al. |
| 2009/0281592 A1 | 11/2009 | Vase |
| 2010/0023000 A1 | 1/2010 | Stevenson et al. |

* cited by examiner

ADAPTATION PROBE FOR INSERTION INTO IMPLANTED ELECTRODE DEVICES OF ACTIVE MEDICAL IMPLANTS AND SET COMPOSED OF AN IMPLANTABLE ELECTRODE DEVICE AND AN ADAPTATION PROBE

This application takes priority from German Patent Application DE 10 2010 000 368.9, filed 11 Feb. 2010, German Patent Application DE 10 2010 000 370.0, filed 11 Feb. 2010, German Patent Application DE 10 2010 000 371.9, filed 11 Feb. 2010, German Patent Application DE 10 2010 000 372.7, filed 11 Feb. 2010, the specifications of which are all hereby incorporated herein by reference.

BACKGROUND OF THE INVENTION

1. Field of the Invention

One or more embodiments of the invention relates to an adaptation probe for insertion into implanted electrode devices of active medical implants to enable them for use in high-frequency magnetic alternating fields of MRI systems. Embodiments of the invention furthermore relate to a set composed of such an implantable electrode device and an adaptation probe that can be inserted therein.

2. Description of the Related Art

Regarding the background of the invention, it should be pointed out that the subject matter of one or more embodiments of the invention is relevant primarily in conjunction with cardiac pacemakers, implantable defibrillators, and other types of active implantable electromedical devices. The latter typically comprise at least one current/voltage-carrying supply lead in the electrode device—typically referred to simply as "electrode"—, the distal end of which is disposed e.g. in a ventricle and is used to measure cardiological potential signals or to transmit relevant therapeutic current signals.

The compatibility of such electrode devices in the case of implantable electromedical devices having high-frequency magnetic fields of the type used in imaging diagnostic methods in particular which are based on magnetic resonance—so-called MRI (magnetic resonance imaging) methods—is a serious problem. In the case of such MRI methods, a magnetic alternating field puled with radio frequency (RF) is superimposed on a strong static magnetic field, which is used to change the energy status of the protons in the tissue being investigated and to produce corresponding MRI signals from the tissue.

Due to the laws of electromagnetic induction, this magnetic alternating field induces alternative voltages in the supply lead of the electrode devices—under discussion here—of electromedical device implants, the energy of which is converted to heat at the electrically conductive contact poles, in particular, of the electrode device with human tissue. This can result in considerable heating e.g. of the tip contact of a cardiac electrode with corresponding impairment and even damage of the cardiac tissue in contact therewith or that surrounds it.

To prevent these problems, U.S. Pat. No. 7,363,090 B2 proposes the use of filters on the basis of oscillating circuits of parallel-connected coil and capacitor, which is assigned to the corresponding supply lead for the tip contact pole or a ring contact pole of a corresponding electrode of an implantable electromedical device. The filters disclosed in this known patent are designed—in practical application by the patent owner—as relatively voluminous components that reinforce the electrode device along a certain length and impart unfavorable mechanical properties to the electrode equipped therewith. Furthermore, the filter is accommodated in a closed housing that does not provide passage for the guide wires that are typically used when implanting an electrode. To this extent, the potential uses of this known electrode with filter devices is limited.

Document US 2009/0281592 A1 makes known filter components for reducing the heating of pacemaker electrodes of an electromedical implant due to the effect of high-frequency magnetic fields produced during MRI procedures, in which case an induction coil is installed around a non-conductive central section of a shank which connects a tip contact pole to an inner spiral conductor of the electrode device. By installing an induction coil on the shank, inductive signal filtering is achieved to reduce the electrode tip without the need for a relatively long, voluminous coil body along the length of the electrode. Capacitive elements can also be integrated in the shank to create an LC filter circuit. As an alternative thereto, a so-called "air coil" is disclosed in this publication as an inductive element, in the case of which the shank may be omitted.

A disadvantage of the prior art described is the fact that such electrode devices must be equipped individually, according to their design, with the appropriate circuits to implement a filter function at the production stage. Conventional electrode devices without such protective devices and, in particular, those that are already implanted in a patient without the appropriate filter devices pose a risk when introduced into a high-frequency magnetic field.

BRIEF SUMMARY OF THE INVENTION

Proceeding therefrom, the problem addressed by embodiments of the invention is that of providing a system which can be used to subsequently reinforce implantable electrode devices of active medical implants such that they are suitable for use in high-frequency magnetic alternating fields, in particular in regard to MRI systems.

This problem is solved by the adaptation probe claimed herein, which comprises an elongated, flexible probe body and an electrical assembly having at least one or more electrical components in the probe body, which are connected to an interface. After the probe body has been inserted into the electrode device that is present, this electrical assembly can be electrically coupled to one of the supply leads of the electrode device such that the electrical properties of the electrode device can be adapted, in particular the frequency-dependent resistance, impedance, capacitance, or inductance thereof. Such an electrode device is therefore subsequently equipped such that it can be used without reservation in a high-frequency magnetic alternating field. The prevention of high-frequency currents in the supply leads of the electrode device, which are induced accordingly by the alternating field, effectively prevents the electrode device, in particular the contact poles thereof, from heating up. The adaptation probe is typically installed after the electrode device has been implanted, in order to change the electrical properties thereof. This has the particular advantage that the electrode device itself is not stiffened locally by the filter elements. The electrode device can therefore be implanted in a particularly gentle manner. The lumen thereof, which is typically provided for a guide wire, can then be used to insert the adaptation probe therein.

According to a preferred embodiment, the probe body can be formed by an insulated wire or a plastic rod which may be optionally equipped with a wire core. Electronic components are then installed on this probe body and are mounted such that they form an electronic component at the functionally desired longitudinal position of the adaptation probe. It can be integrated into the probe body e.g. before the tip of the adaptation probe and/or at, at least two, or preferably several longitudinal positions of the probe body. The tip of the probe body can be designed to be electrically conductive or insulating.

According to a preferred embodiment, each of the electrical components can be coupled to the electrode device by way of one or more connection contacts. This can be a direct electrical contact, or a capacitative or inductive coupling to the supply lead or corresponding components of the electrode device is also feasible.

The contact connection can be designed according to various concepts, for example, the connection contact can be connected to a supply lead of the electrode device in a form-fit manner, or can be designed geometrically and physically as contact spring, sliding contact, or a similar contact tab. For a subsequent reinforcement of an implanted electrode device, a preferred embodiment is particularly advantageous in which one or more electrical assemblies are detachably fastened to the probe body, in particular on the tip thereof. Therefore, the electrical assembly can be "released" after the adaptation probe with the electrical assembly/assemblies thereof have been inserted into the electrode device and the suitable contact with the supply lead thereof has been established. In this regard, the actual probe body does not need to remain in the electrode device. Only the assembly that adapts the electrical properties of the electrode device remains permanently at the site. According to a related embodiment of the connection between electrical assembly and probe body, e.g. in the form of a bayonet connection, the electrical assembly can also be removed from the electrode device by reinserting the probe body and attaching the electrical assembly thereto.

Further preferred embodiments relate to the embodiment of the electrical assembly itself, which can comprise e.g. electrical contact pins with miniature electronic components connected therebetween. Contact pins and miniature components are all disposed together in a bonded manner in a filter housing applied by injection molding all around. According to another embodiment, a "barrel filter" is provided as the electrical assembly, in which the contact pins of the electrical assembly are designed as mutually insulated caps that face one another, in the interior of which the electrical components of the electrical assembly are disposed.

Since the adaptation probe can be used in various electrode devices, it is particularly advantageous if the electrical assembly can be adjusted individually by way of series- and/or parallel-connected filter elements by bridging them with separable short-circuit lines. The bridged element is activated by separating a particular line.

Finally, one or more embodiments of the invention relates to a set composed of an implantable electrode device of a medical implant and an adaptation probe which can be inserted therein is designed according to one of the embodiments described above.

In summary, the adaptation probe according to the invention is a particularly simple solution for enabling conventional electrical devices of active medical implants to be used in high-frequency magnetic alternating fields. The actual design of the electrode device does not need to be changed. The adaptation probe is a universal solution for different types of electrodes. Heating of the electrode device is reliably prevented nevertheless, and the cardiac muscle is not damaged by heating of the contact poles of the electrode device in the MR environment. Finally, a further advantage of the adaptation probe is that space that was previously left unused, namely the lumen provided only to receive the guide wire during implantation of the electrode device, is used to accommodate the electrical assembly.

BRIEF DESCRIPTION OF THE DRAWINGS

Further features, details, and advantages of the invention will be apparent from the description of embodiments, which follows, and with reference to the attached drawings. In the drawings.

DETAILED DESCRIPTION OF THE INVENTION

Figure 1:
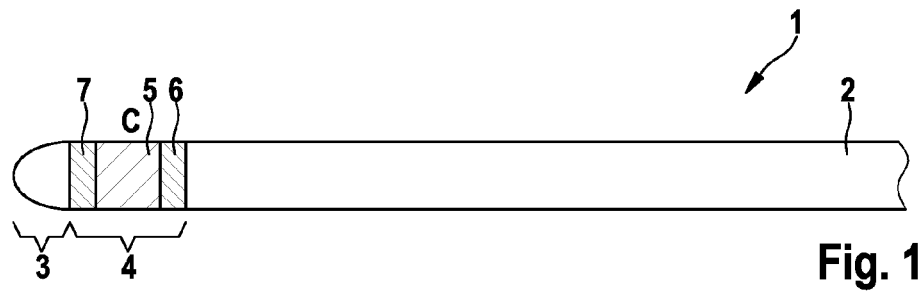
FIGS. 1 to 3 show schematic side views of sections of an adaptation probe to be inserted into an electrode device, in different embodiments.

The basic configuration of an adaptation probe 1, which is also referred to as a "finishing wire", will be explained in greater detail with reference to FIG. 1. A probe body 2 is formed of an elongated, flexible plastic rod equipped with a metal core which is not depicted. Shortly before distal tip 3, which is likewise non-conductive in the case shown, an electrical assembly 4 which can be composed e.g. of a capacitor 5 having a related capacitance C is integrated into probe body 1. This capacitor is to be electrically connected to a supply lead of the electrode device by way of connection contacts 6, 7 in a manner to be described in greater detail.

Figure 2:
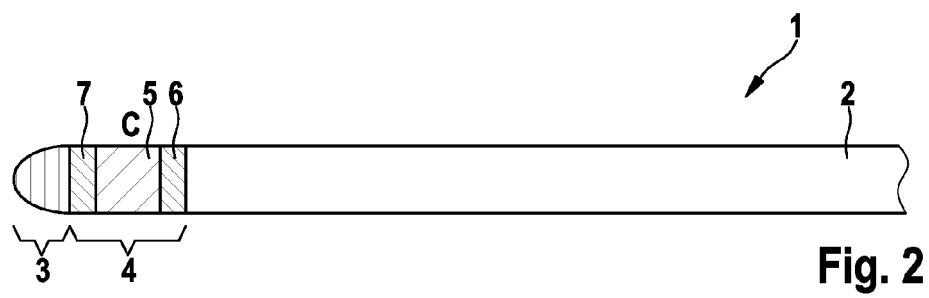

In the case of the embodiment shown in FIG. 2, tip 3 in front of the electrical assembly 4 is conductive.

Figure 3:
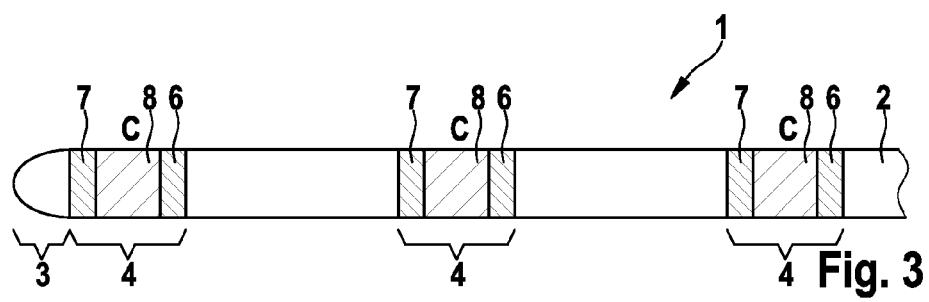

FIG. 3 shows an adaptation probe 1, in the case of which a plurality of electrical assemblies 4 having electrical components 8, such as capacitors or even more complex circuits, are integrated therein, being distributed over a plurality of longitudinal positions of probe body 2.

Figure 4:
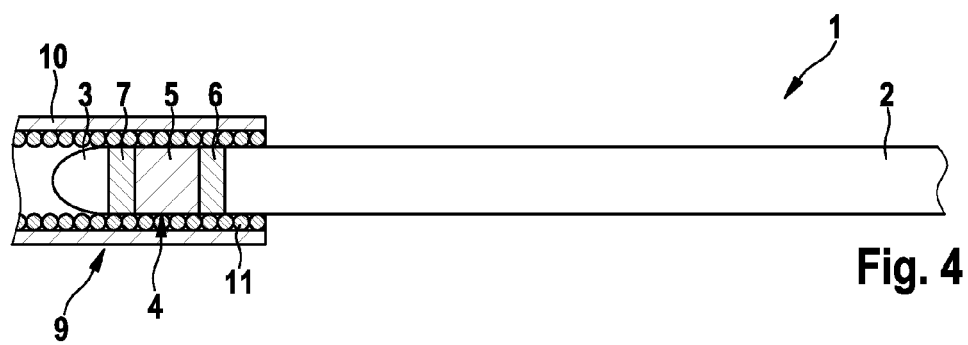
FIG. 4 shows an adaptation probe in a state in which it has been inserted into an electrode device.

FIG. 4 shows the basic principle of cooperation between adaptation probe 1 and electrode device 9 which is shown in sections in this drawing. Electrode device 9 is shown with electrode body 10 thereof and a spiral supply lead 11 which extends therein to a contact pole which is not shown. Adaptation probe 1 slid into lumen 12 of electrode device 9 and contacts spiral supply lead 11 at a suitable point. Between the two connection contacts 6, 7 of electrical assembly 4, the spiral supply lead functions as inductance and, together with capacitor 5 in adaptation probe 1, can therefore form an LC oscillating circuit having a typical frequency-dependent transmission behavior. When adapted accordingly, the currents induced in the supply lead, which occur in the electrode device due to a high-frequency alternating field in the MR environment, are filtered out.

Figure 5:
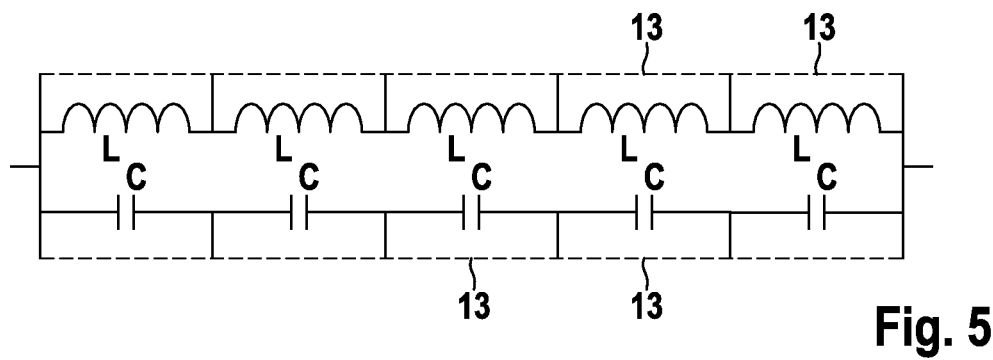
FIG. 5 shows a wiring diagram of an electrical assembly having an adjustable frequency behavior.

FIG. 5 shows an electrical assembly in the form of an adjustable filter, in which a series circuit of inductances L is connected parallel to a series circuit of capacitances C. Each inductance L and capacitance C itself is short-circuited by jumpers 513 which—as indicated using dashed lines—can be separated individually. It is therefore possible to include the desired number of inductances L and/or capacitances C to the oscillating circuit with corresponding total inductance $L_{ges}$ and total capacitance $C_{ges}$. In this manner, a potential scattering of the filter characteristics can be compensated for during production. "Trimming" takes place by changing the capacitances and/or inductances.

Figure 6:
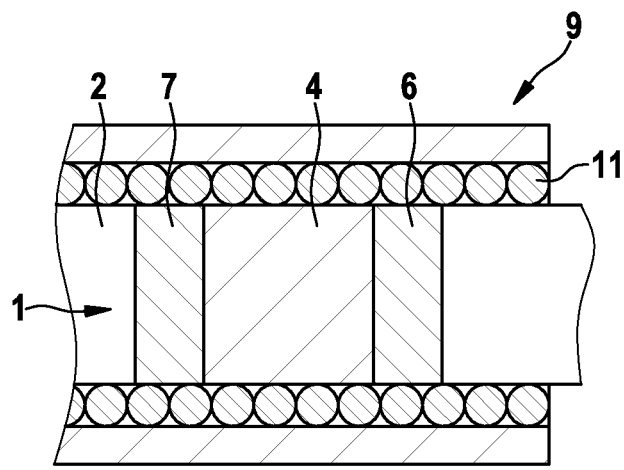
FIGS. 6 and 7 show views of the contacting between an electrical assembly of an adaptation probe and the electrode device in two variants thereof.

Other alternatives for the contacting between electrical assembly 4 and supply lead 11 will be explained with reference to FIGS. 6 and 7. FIG. 6 shows a form-fit contacting in which probe body 2 with annular connection contacts 6, 7 is slid into the lumen of spiral supply lead 11, thereby contacting the corresponding winding of spiral supply lead 11 which is bare at this point.

Figure 7:
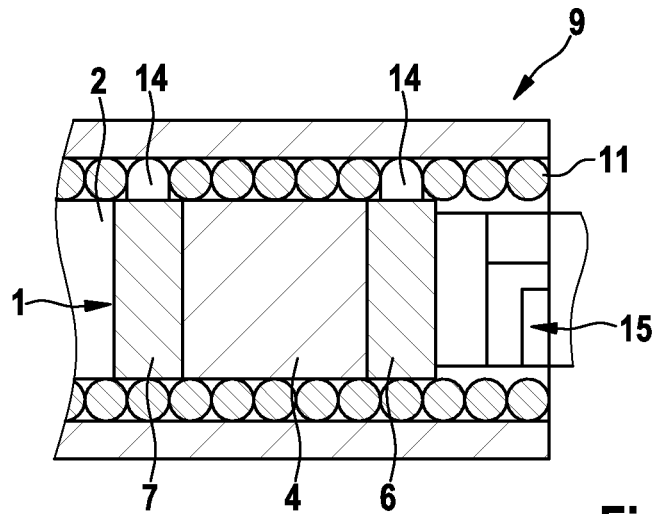

In the embodiment shown in FIG. 7, contacts 6, 7 have geometric shapes e.g. in that a laterally projecting contact spring 514 establishes the electrical connection between connection contacts 6, 7 and spiral supply lead 11 at two different positions.

FIG. 7 also shows a bayonet connection 15, which indicates that in this embodiment the distal end section of adaptation probe 1 was "released" in electrode device 9 and remaining probe body 2 was removed.

FIGS. 8 to 15 show different embodiments of how electrical assemblies 4 can be designed in the form of high-frequency filter 21 which is suitable for insertion into an electrode device for a cardiac pacemaker, defibrillator, neurostimulator or similar active medical implants.

Housings of aforementioned filters are typically composed of solid metal parts, and expensive ceramic components are usually used to build an insulation between housing and electrical components. The sealing of the housing is very elaborate, problematic, and therefore cost-intensive. The concepts shown in FIGS. 8 to 11 make it possible to create a simply designed seal against fluids, thereby enabling high frequency filter 21 to be realized in a cost-favorable manner. Highly diverse electrical components can be embedded easily and in a variable manner since the housing is created mainly by providing a coating applied by injection molding, and possibly various pre- and post-handling steps.

Figure 8:
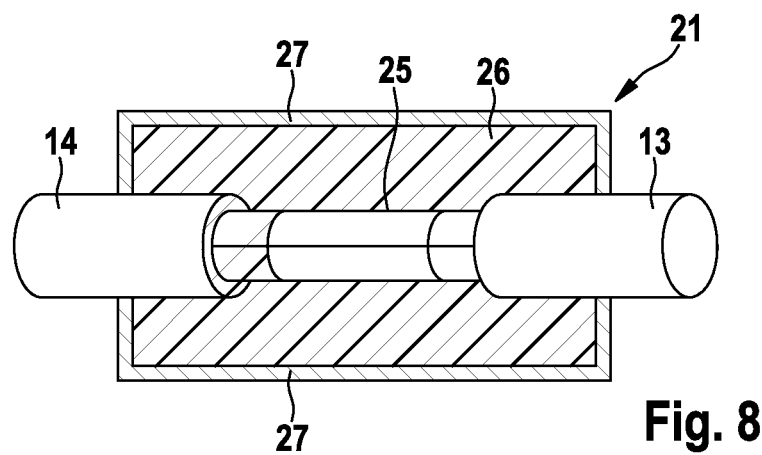
FIGS. 8 to 15 show highly schematicized depictions of electrical assemblies in the form of high-frequency filters in various embodiments.

In detail, FIG. 8 shows contact pins 13, 14 of filter 21, which are interspaced collinearly, between which one or more electrical components 25 are installed, being interconnected accordingly, and thereby being connected. The ends of contact pins 13, 14 are left exposed and this entire assembly is enclosed in a plastic body 26 applied by injection molding, which ensures that components 25 are sealed and electrically insulated.

If necessary, filter 21 produced in this manner can also be provided with a coating 27 which can be composed e.g. of a plastic, a ceramic, or another type of anorganic layer. Such a functional coating 27 is used to adapt the surface properties to particular usage conditions; for example, coating 27 can provide mechanical stabilization or form a vapor barrier.

Figure 9:
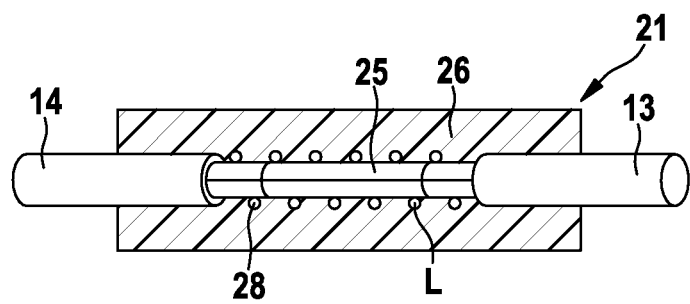

The embodiment depicted in FIG. 9 differs from that shown in FIG. 8 in that a wire coil 28 is also wound around electrical components 25 between contact pins 13, 14, which can generate inductance L of high frequency filter 21.

Figure 10:
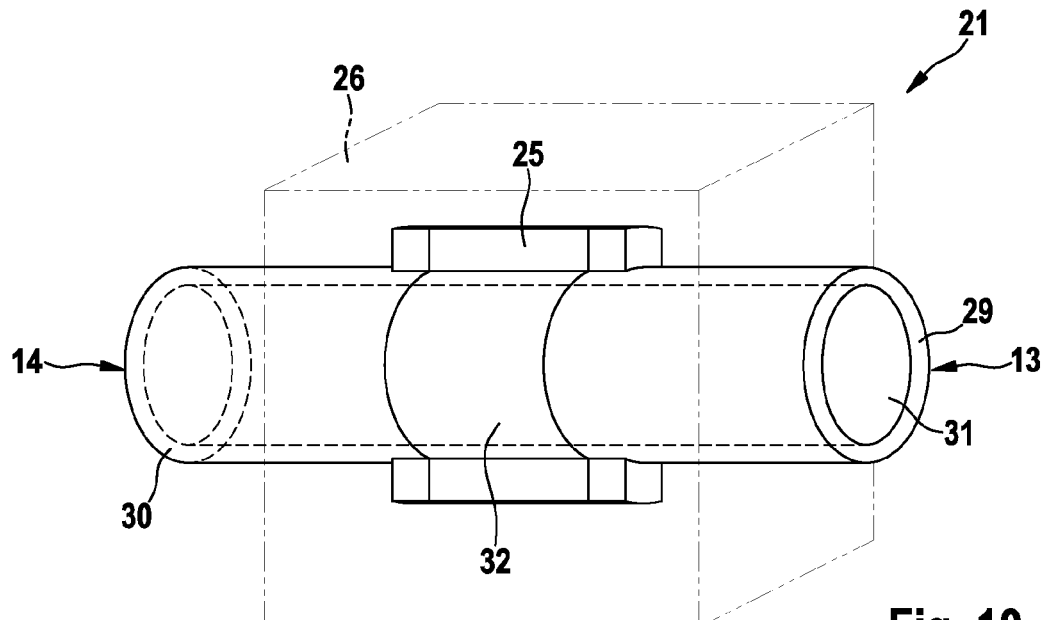

To provide an adaptation probe 1 with a high frequency filter 21 and simultaneously enable the use of a guide wire, FIG. 10 shows an embodiment in which contact pins 13, 14 are designed as conductive tubes 29, 30, lumen 31 of which align with a corresponding passage 32 in plastic body 26 that forms filter housing 22. A guide wire, mandrel, or the like can then pass through lumen 31 and passage 32. As shown clearly in FIG. 10, electrical components 25 are embedded such that they are offset laterally relative to passage 32.

Figure 11:
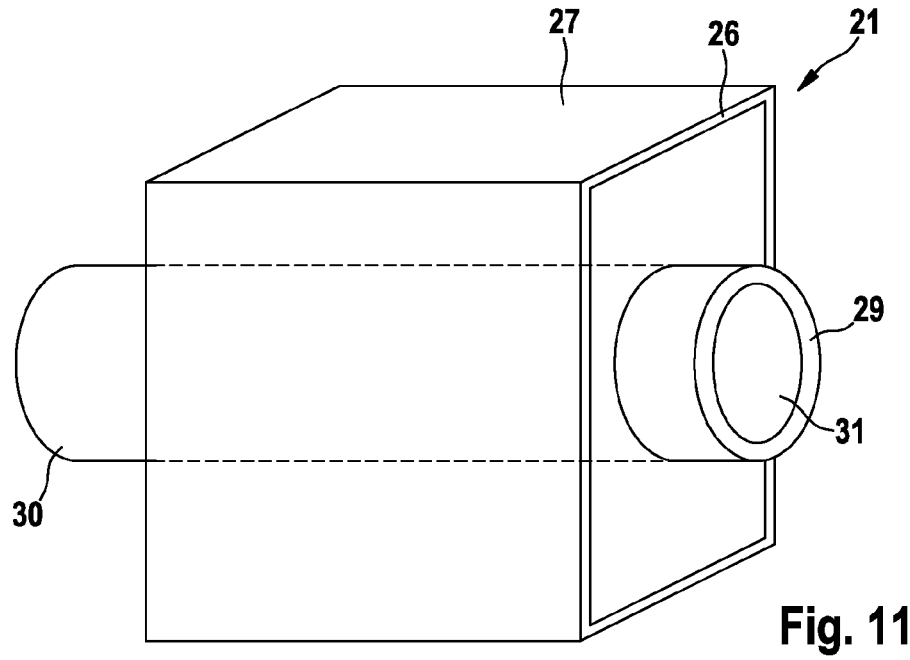

FIG. 11 shows another outer view of the filter depicted in FIG. 10, in which case as well a coating 27 of metal, various plastics or anorganic or organic compounds depending on the desired functionality is applied to the housing.

Electrical contact pins 13, 14 or tubes 29, 30 can be composed of stainless steel, platinum, platinum/iridium alloy, or titanium. They may also be provided with one or more bores, grooves, engravings, or recesses to increase the mechanical strength of filter 21 after the coating is applied by injection molding, thereby stabilizing it overall.

FIGS. 12 to 17 which follow show embodiments of a high frequency filter 21 that do not require contact pins, and the housing of which can therefore be sealed in a simple manner. In the case of the above-described variants of filter 21, contact pins 13, 14 increase the overall size of filter 21, and additional passages must be insulated or sealed off.

Figure 12:
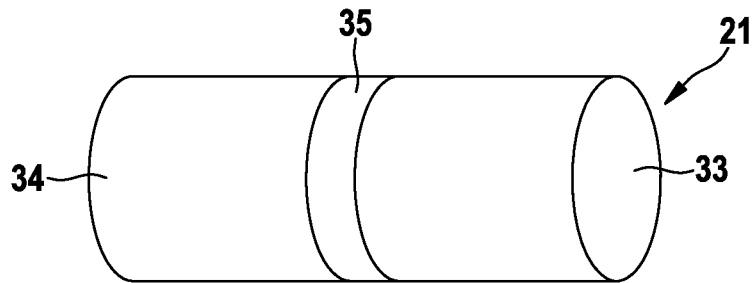
Figure 13:
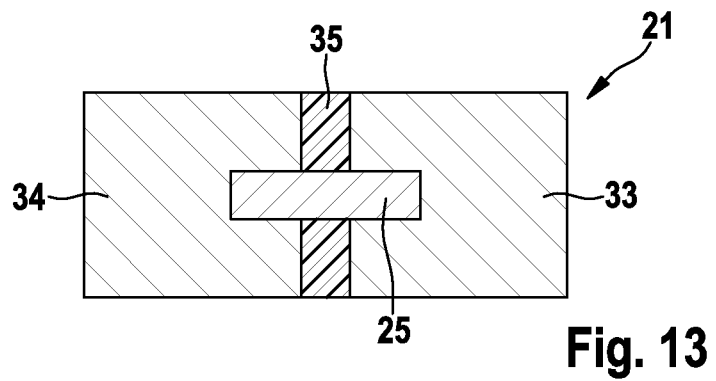

As made clear from the view according to FIG. 12 and the schematic sectional view according to FIG. 13, the contact pins are formed by two contact caps 33, 34 which are insulated from one another, and which are mechanically connected and electrically insulated by an insulator insert 35. The two "semi-barrels" formed by contact caps 33, 34 are connected in a water-tight manner, and two electrically separated regions result.

Figure 14:
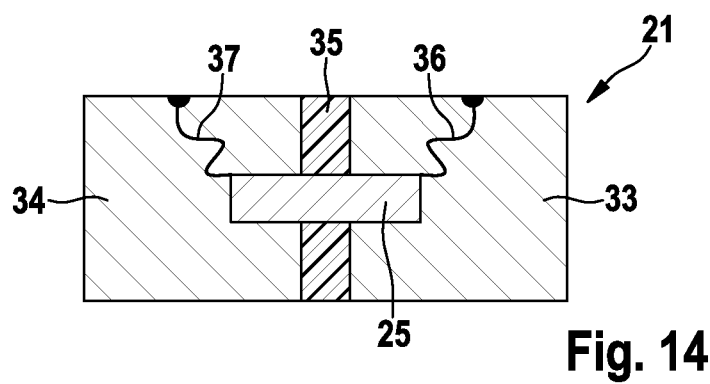

Electrical components 25 are arranged in insulator insert 35 in an appropriate configuration so that they have e.g. a high-pass, low-pass, bandpass, or band-stop behavior. Electrical components 25 are electrically connected to the inside of contact caps 33 and 34. As indicated in FIG. 14, this takes place via appropriate connecting lines 36, 37 which are formed by typical wires, litz wires, or wire cables, and can be welded, crimped, or lased to the inside of contact caps 33, 34. An inductively or capacitively coupling connection of the connectors is also feasible.

The embodiment of high frequency filter 21 as a barrel filter described herein results in a shortening of the overall size and increases safety by reducing connection points. When installed in an adaptation probe, the region stiffened by the filter is therefore shortened as well.

Figure 15:
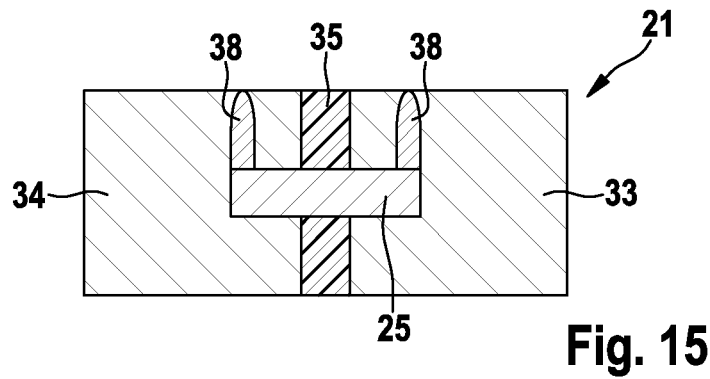

As shown in FIG. 15, components 25 can also be electrically contacted via sliding contacts 38 or corresponding contact springs which are in electrical contact with the inner side of contact caps 33 and 34.

Figure 16:
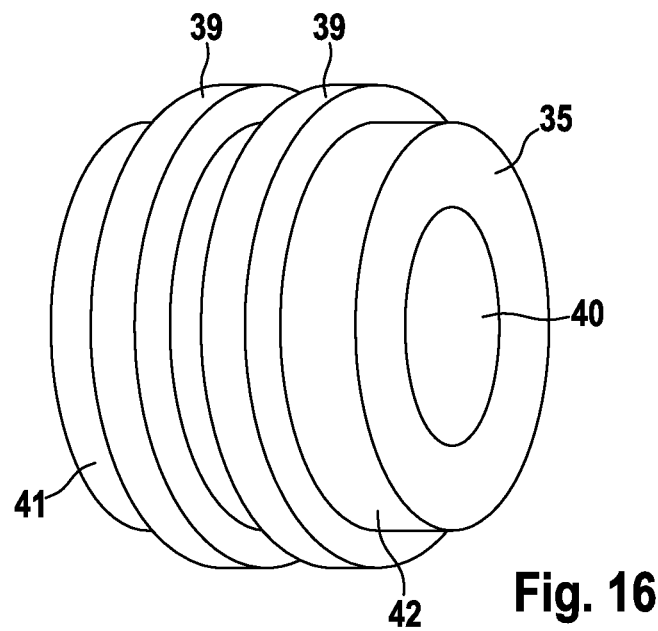
FIGS. 16 and 17 show partial depictions of such high-frequency filters.
Figure 17:
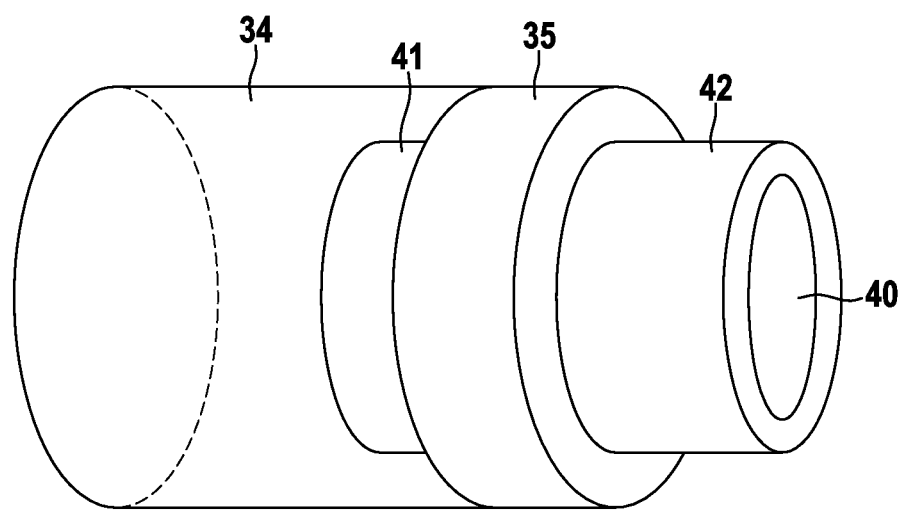

FIG. 16 shows a special embodiment of insulator insert 35, on which a welding disc 39 composed of metal has been placed. They extend radially beyond the jacket wall of cylindrical insulator insert 35 and are used to connect contact caps 33, 34 by welding. Furthermore, insulator insert 35 has a passage coaxially in the center, similar to a tube, in the form of a bore or the like, as a recess for components 25.

Figure 21:
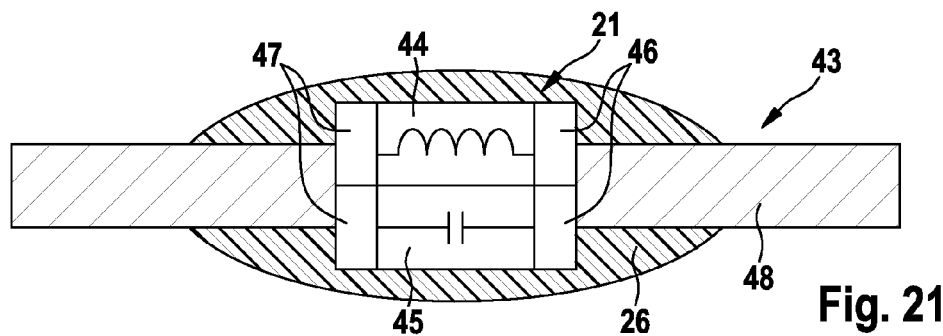

Insulator insert 35, as insulating intermediate piece, can be composed e.g. of ceramic or plastic, onto corresponding projections 41, 42 of which the contact caps—left contact cap 34 is shown in FIG. 21—can be slid and fastened to insulator insert 35 by welding, soldering, bonding, crimping, or the like.

Instead of metal, the two semi-barrels of contact caps 33, 34 can also be made of a plastic, a conductive plastic, a ceramic, or another non-conductor. They must then be coated entirely or partially with a conductive material.

Finally, FIGS. 18 to 26 relate to further integral designs of a high-frequency filter 21.

Figure 18:
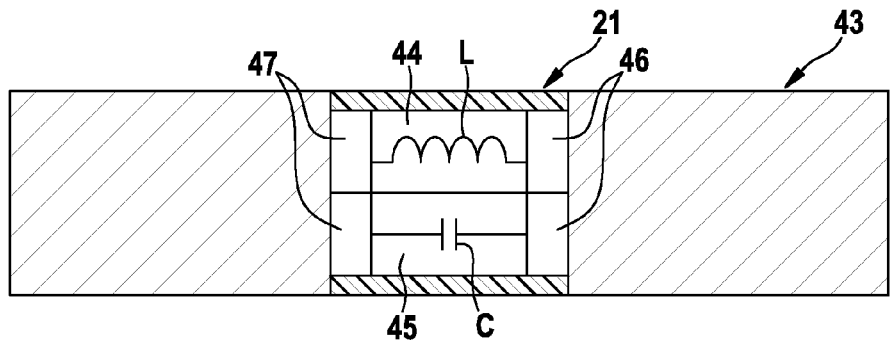
FIGS. 18 to 26 show schematic coaxial longitudinal sectional views of electrical assemblies having integrated high-frequency filters in different embodiments.

For example, FIG. 18 shows a high-frequency filter element 21 as pin unit 43, in which a filter composed of two SMD components 44, 45 in the form of inductance L and capacitance C connected in parallel is formed. The design of SMD components 44, 45 need not be identical. They are integrated completely in the pin unit, which can therefore be manufactured isodiametrically. Connectors 46, 47 to the left and right are composed of conductive material.

Figure 19:
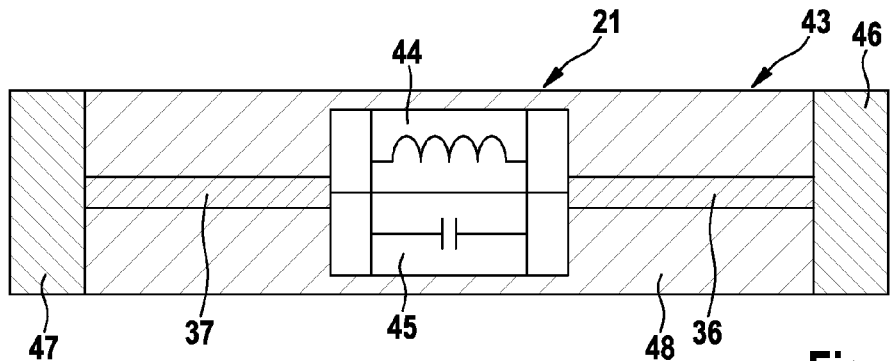

As shown in FIG. 19, pin unit 43 can also be composed of a body 48 of dielectric material, which has corresponding connecting lines 36, 37 between SMD components 44, 45, which form the filter components, and connectors 46, 47. This design places less of a demand on the filter components since they are embedded in a homogeneous material.

Figure 20:
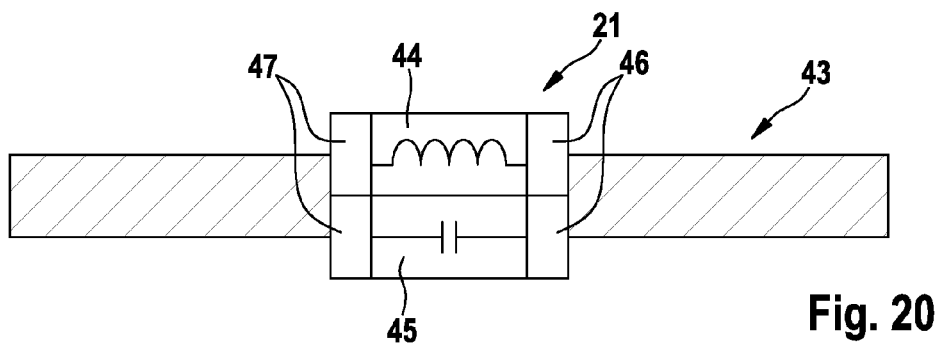

In the embodiment shown in FIG. 20, high frequency filter 21 and SMD components 44, 45 thereof are integrated in a body 48 having a relatively thin structure. This installation between two conductive elements is omitted in this drawing. Entire pin unit 43 is therefore not necessarily isodiametrical. As described with reference to FIG. 19, this embodiment can also be composed of dielectric material having suitable lead structures.

To separate high frequency filter 21 itself from the surroundings, it is enclosed in a plastic body 26 applied by injection molding, a coating, a housing, or a similar measure, as shown in FIG. 21.

Figure 22:
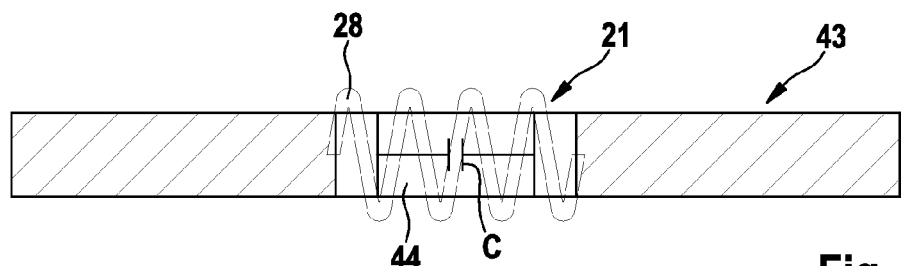
Figure 23:
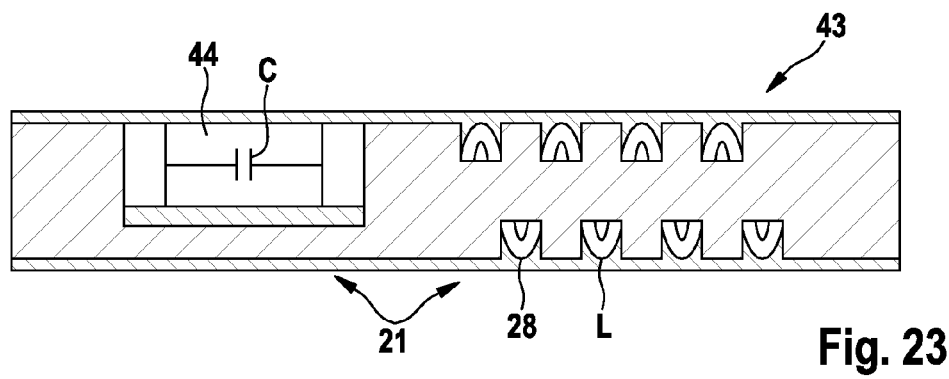

A further miniaturization for pin unit 43 is attained using the embodiment shown in FIG. 22. There, wire-wound coil 28 of high frequency filter 21 is placed around SMD component 44 which is designed as capacitor C. The required space is therefore markedly reduced compared to the above-described embodiments according to FIGS. 18 to 21.

Figure 24:
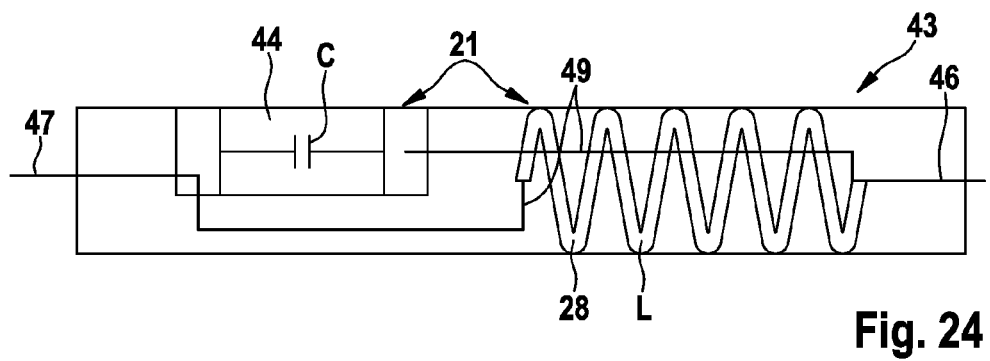

In the embodiment of pin unit 43 depicted in FIG. 28, coil 24 and SMD component 44 for capacitance C are installed mechanically one behind the other, wherein interconnection 49 emphasized using solid lines is parallel. The pin unit can be isodiametric in design and comprise appropriate connectors 46,47 on the ends thereof. In the interior of the component, capacitance C is installed as capacitor SMD component 44, and inductance L is installed as wire-wound coil. In FIG. 24, the supporting structure of the body of the pin unit is omitted for clarity.

Figure 25:
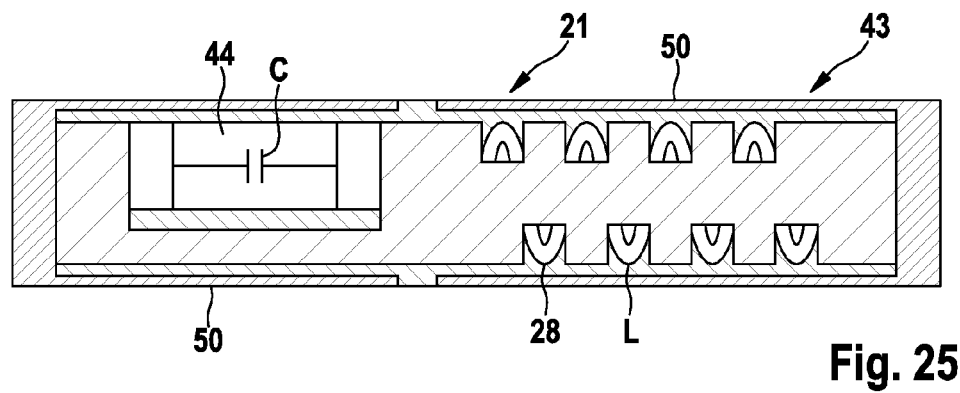
Figure 26:
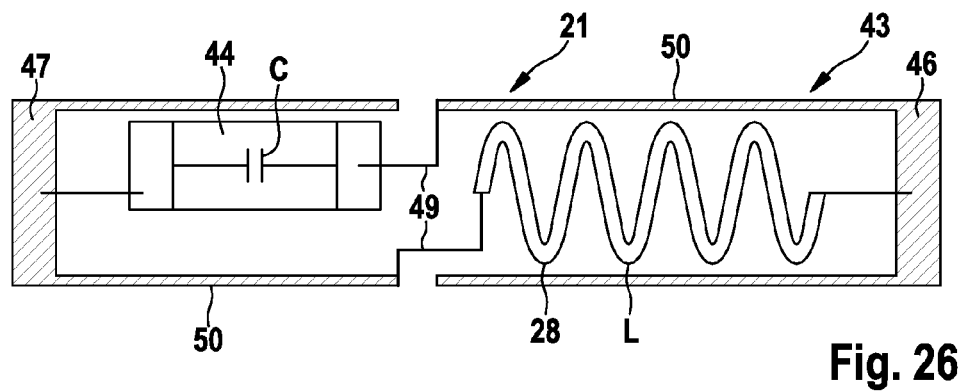

Such a supporting structure is shown in FIG. 25. Furthermore, this embodiment comprises a metallization 50 which extends over wide subregions of pin unit 43 on the outer side thereof. The contacting of the components takes place via metallization 50, namely that of wire-wound coil 28 and capacitor SMD component 44, as shown in FIG. 26. Interconnection 49 can therefore be designed with shorter paths in the interior.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE CHARACTERS

1 Adaptation probe
2 Probe body
3 Tip-distal
4 Electrical assembly
5 Capacitor
6 Connection contact
7 Connection contact
8 Electrical component
9 Electrode device
10 Electrode body
11 Spiral supply lead
12 Lumen
13 Contact pin
14 Contact pin
15 Bayonett connection
25 Electrical components
26 Plastic body
27 Coating
28 Wire-wound coil
29 Tube
30 Tube
31 Lumen
32 Passage
33 Contact cap
34 Contact cap
35 Insulator insert
36 Connecting line
37 Connecting line
38 Sliding contact
39 Welding disc
40 Passage
41 Projection
42 Projection
43 Pin unit
44 SMD component
45 SMD component
46 Connector
47 Connector
48 Body
49 Interconnection
50 Metallization
513 Jumper
514 Contact spring

What is claimed is:

1. An adaptation probe for insertion into implanted electrode devices of active medical implants for use in high-frequency magnetic alternating fields of MRI systems comprising:
    a probe body that is elongated and flexible and configured to fit within a lumen of an electrode device; and,
    at least one electrical assembly coupled within said probe body comprising an interface;
        one or more electrical components connected to said interface wherein said one or more electrical components are configured to be electrically coupled to one supply lead of a plurality of supply leads of the electrode device such that electrical properties of the electrode device are configurable, wherein said electrical properties comprises any combination of one or more of frequency-dependent resistance, impedance, capacitance, or inductance thereof; and,
        a plurality of electrical contact pins comprising miniature electronic components connected therebetween, wherein the plurality of contact pins and the miniature components are all configured to be enclosed in a filter housing;
    a wire coil wound between the plurality of contact pins around the miniature electrical components configured to generate an inductance L of a high frequency filter in the filter housing.

2. The adaptation probe according to claim 1, wherein the probe body comprises
    an insulated wire or a plastic rod;
    or
    an insulated wire or a plastic rod equipped with a wire core.

3. The adaptation probe according to claim 1, wherein the adaptation probe comprises a tip and wherein the at least one electrical assembly coupled within the adaptation probe body is integrated into the probe body before said tip.

4. The adaptation probe according to claim 1, wherein the at least one electrical assembly is integrated into the probe body at, at least two or more longitudinal positions of the probe body.

5. The adaptation probe according to claim 1, wherein the adaptation probe comprises a tip and wherein the tip of the probe body is electrically conductive or insulating.

6. The adaptation probe according to claim 1, wherein the at least one electrical assembly comprises at least one connection contact and wherein said at least one electrical assembly is configured to connect to said electrode device via said at least one connection contact.

7. The adaptation probe according to claim 6, wherein the connection contact is configured to connect to said one of said supply leads of the electrode device in a form-fit manner.

8. The adaptation probe according to claim 6, wherein the at least one connection contact comprises a contact spring, sliding contact, or contact tab.

9. The adaptation probe according to claim 6, wherein the adaptation probe comprises a tip and wherein the at least one electrical assembly is detachably coupled to the probe body, on the tip thereof.

10. The adaptation probe according to claim 1, wherein the adaptation probe comprises a tip and wherein the at least one electrical assembly is detachably attached to the probe body at the tip thereof.

11. The adaptation probe according to claim 10, further comprising a bayonet connection, wherein the at least one electrical assembly can be detached from and reattached to the probe body via the bayonet connection.

12. The adaptation probe according to claim 1, wherein the contact pins of the at least one electrical assembly comprise mutually insulated caps each with an interior, wherein the mutually insulated caps face one another, and the one or more electrical components of the electrical assembly are disposed in the interior.

13. The adaptation probe of claim 12, wherein said adaptation probe further comprises an insulator insert, wherein said insulator insert is an insulating intermediate piece entirely located between said caps, and wherein each of said caps are mechanically connected by said insulator insert and each of said caps are insulated from one another by said insulator insert.

14. The adaptation probe of claim 13, wherein said insulator insert comprises a centered coaxial passage, such that said electrical components are arranged in said insulator insert via said centered coaxial passage.

15. The adaptation probe according to claim 1, wherein the at least one electrical assembly comprises series- and/or parallel-connected filter elements (L, C) which are bridged by separable short-circuit lines, wherein said separable short-circuit lines comprise jumpers.

16. The adaptation probe of claim 1, wherein each of said plurality of contact pins comprise a conductive tube and a contact pin lumen.

17. An adaptation probe for insertion into implanted electrode devices of active medical implants for use in high-frequency magnetic alternating fields of MRI systems comprising:
  a probe body that is elongated and flexible and configured to fit within a lumen of an electrode;
  at least one electrical assembly coupled with said probe body comprising
    an interface;
    one or more electrical components connected to said interface wherein said one or more electrical components are configured to be electrically coupled to one supply lead of a plurality of supply leads of an electrode device such that electrical properties of the electrode device are configurable, wherein said electrical properties comprises any combination of one or more of frequency-dependent resistance, impedance, capacitance, or inductance thereof;
    a plurality of electrical contact pins comprising miniature electronic components connected therebetween, wherein the plurality of contact pins and the miniature components are all configured to be enclosed in a filter housing;
    a wire coil wound between the plurality of contact pins around the miniature electrical components configured to generate an inductance L of a high frequency filter in the filter housing;
    wherein the contact pins of the at least one electrical assembly comprise mutually insulated caps each with an interior, wherein the mutually insulated caps face one another, and the one or more electrical components of the electrical assembly are disposed in the interior; and
    wherein said adaptation probe further comprises an insulator insert, wherein said insulator insert is an insulating intermediate piece entirely located between said caps, and wherein each of said caps are mechanically connected by said insulator insert and each of said caps are insulated from one another by said insulator insert.

18. A set composed of an implantable electrode device of an active medical implant and an adaptation probe which can be inserted therein for insertion into the implantable electrode device for use in high-frequency magnetic alternating fields of MRI systems comprising:
  a probe body that is elongated and flexible and configured to fit within a lumen of an electrode;
  at least one electrical assembly coupled with said probe body comprising
    an interface;
    one or more electrical components connected to said interface wherein said one or more electrical components are configured to be electrically coupled to one supply lead of a plurality of supply leads of an electrode device such that electrical properties of the electrode device are configurable, wherein said electrical properties comprises any combination of one or more of frequency-dependent resistance, impedance, capacitance, or inductance thereof;
    a plurality of electrical contact pins comprising miniature electronic components connected therebetween, wherein the plurality of contact pins and the miniature components are all configured to be enclosed in a filter housing;
    a wire coil wound between the plurality of contact pins around the miniature electrical components configured to generate an inductance L of a high frequency filter in the filter housing;
    wherein the contact pins of the at least one electrical assembly comprise mutually insulated caps each with an interior, wherein the mutually insulated caps face one another, and the one or more electrical components of the electrical assembly are disposed in the interior; and wherein said adaptation probe further comprises an insulator insert, wherein said insulator insert is an insulating intermediate piece entirely located between said caps, and wherein each of said caps are mechanically connected by said insulator insert and each of said caps are insulated from one another by said insulator insert.

\* \* \* \* \*